(12) United States Patent
Grey et al.

(10) Patent No.: US 7,477,382 B2
(45) Date of Patent: Jan. 13, 2009

(54) ATOMIC ABSORPTION SPECTROMETER

(75) Inventors: Ronald G Grey, Beaumaris (AU); Peter J Saunders, Box Hill North (AU)

(73) Assignee: GBC Scientific Equipment Pty Ltd (AU)

( * ) Notice: Subject to any disclaimer, the term of this patent is extended or adjusted under 35 U.S.C. 154(b) by 193 days.

(21) Appl. No.: 11/522,573

(22) Filed: Sep. 18, 2006

(65) Prior Publication Data
US 2007/0008527 A1      Jan. 11, 2007

Related U.S. Application Data

(62) Division of application No. 10/484,489, filed as application No. PCT/AU02/01079 on Aug. 6, 2002, now Pat. No. 7,133,131.

(30) Foreign Application Priority Data

Aug. 10, 2001   (AU)   .................... PR6945
Oct. 17, 2001   (AU)   .................... PR8335

(51) Int. Cl.
*G01J 3/12*       (2006.01)
*G01J 3/30*       (2006.01)
(52) U.S. Cl. .................... 356/331; 356/311; 356/312; 356/326
(58) Field of Classification Search ......... 356/331–334, 356/326, 328, 311, 312, 319, 310, 307
See application file for complete search history.

(56) References Cited

U.S. PATENT DOCUMENTS

| | | | |
|---|---|---|---|
| 3,917,407 A | 11/1975 | Newstead | |
| 3,924,950 A * | 12/1975 | Siegler, Jr. | 356/307 |
| 4,976,541 A | 12/1990 | Scuitto et al. | |
| 4,991,960 A | 2/1991 | Huber et al. | |
| 5,166,755 A * | 11/1992 | Gat | 356/419 |
| 5,594,547 A | 1/1997 | Rodel et al. | |
| 6,222,626 B1 * | 4/2001 | Radziuk et al. | 356/307 |
| 6,870,619 B1 * | 3/2005 | Tenhunen et al. | 356/330 |

FOREIGN PATENT DOCUMENTS

AU        18889/88 A        1/1989

* cited by examiner

*Primary Examiner*—L. G Lauchman
(74) *Attorney, Agent, or Firm*—Michael Best & Friedrich LLP

(57) ABSTRACT

An atomic absorption spectrometer is disclosed which includes a monochromater and an optical path defined by a toric mirror, a flat mirror, a flat mirror, a flat mirror, a toric mirror, and a further toric mirror. The toric mirror directs light through entrance slit of the monochromater so that radiation is reflected from diffraction grating and out exit slit to a detector. A sample stage in the form of a furnace is located between the mirrors. The monochromater is oriented so that the entrance slit is arranged transverse to the vertical. In one arrangement, a magnifying means is also provided which magnifies an image of the aperture at the sample station to increase the amount of radiation which is focused at the sample stage, and which is passed through the aperture to the detector or a focusing element provided by one of the mirrors may be provided for focusing radiation at a location other than sample station so an enlarged out of focus image of the entrance slit is produced at the sample station to increase the amount of radiation which passes through the slit and is received by the detector.

9 Claims, 4 Drawing Sheets

ATOMIC ABSORPTION SPECTROMETER

RELATED APPLICATION

This application is a divisional patent application of U.S. patent application Ser. No. 10/484,489, filed on Jan. 19, 2004 now U.S. Pat. No. 7,133,131, which is a 371 of PCT Application No. PCT/AU02/01079, filed on Aug. 6, 2002, the content of which is incorporated herein by reference.

FIELD OF THE INVENTION

This invention relates to an atomic absorption spectrometer.

BACKGROUND ART

Atomic absorption spectrometers are well known and analyse a sample material by directing a beam of electromagnetic radiation through a sample and then detecting absorption of the beam by the sample and therefore the concentration of the sample.

Atomic absorption spectrometers usually carry a carousel of hollow cathode lamps which are selectively placed into alignment with the optical axis of the instrument to enable electromagnetic radiation of a particularly wavelength to be directed to a sample. The optical path of the instrument generally comprises an array of lenses or mirrors and a sample stage interposed in the optical path through which the electromagnetic radiation passes. Electromagnetic radiation is directed to a monochromater which includes a monochromater mirror for reflecting the radiation to a diffraction grating which reflects the radiation back to the mirror. The mirror reflects the radiation to a detector for analysis. The diffraction grating can be moved under computer control to tune the instrument to the particular wavelength which is emitted by the cathode lamp. In general, the instrument will step through a number of analysis steps, each using a different cathode lamp to provide radiation of different wavelength which passes through the sample. The diffraction grating is moved under computer control so as to reflect that wavelength back to the monochromater mirror for reflection to the detector. The absorption of that wavelength by the sample and therefore the lack of detection of that particular wavelength by the detector indicates that the sample does include atoms of a particular type which absorb that wavelength and therefore constituents of the sample can be identified.

The light which enters the monochromater passes through a vertical slit for receipt by the monochromater mirror and after reflection by the diffraction grating, and the monochromater mirror towards the detector, passes through another vertical slit to be received by the detector.

The cathode lamps which produce the radiation generally comprise a 3 mm diameter source which is directed by the optics of the instrument to focus at the sample to provide a 3 mm diameter source image at the sample. The radiation then passes to the slit in the monochromater and passes through the slit into the monochromater. Typically the slit is about 0.25 mm wide. An image of the slit or, in other words, the image which is received by the detector when focused at the source is therefore a vertical slit of about 0.25 mm width. Radiation produced by the cathode tube and which falls outside the perimeter of the slit is therefore not received by the photodetector of the spectrometer, and therefore plays no function in analysis of the sample material. Thus, a significant amount of 3 mm diameter spot of light at the sample stage is lost.

In order to provide sample material for analysis, the spectrometer includes a burner which produces a flame to ionize sample material which is introduced into the flame. The ionized sample material in general is carried up with the flame in the burner and the radiation from the cathode tube is focused in the flame at the sample position so that the radiation, more likely than not, will pass through atoms of the sample material and be absorbed. By detecting absorption of the radiation, the constituents of the sample material can be measured as is described above.

In general, because the sample is ionized in a flame, the atoms of the sample will move upwardly with the flame and will pass through the image of the slit of the monochromater at the sample stage therefore falling within the path of the radiation which passes through the source image and therefore through the slit in the monochromater for detection.

However, if other methods of producing sample material are utilized, the likelihood of the radiation from the source passing through sample atoms can be much less. For example, if sample is produced in a graphite furnace rather than a flame, there is a significant possibility that sample atoms will not locate in the source image of the slit at the sample location and therefore will not fall within the path of the radiation which is actually detected by the detector. Thus, there is a possibility that sample atoms and therefore the true constituent nature of the sample material will not be determined.

Graphite furnaces generally comprise a graphite tube of circular cross-section which is located at the sample stage. The graphite tube is open at both ends and the radiation passes through the tube. High electric current is supplied across the graphite tube to heat the graphite tube and therefore atoms of sample material which is deposited in the tube. In general, the sample material is deposited in the tube by a very thin needle which passes through an aperture or bore in the instrument and through an aperture or bore in the graphite tube. With conventional instruments, considerable skill is required in order to deposit the sample material at a correct location so that when the graphite furnace is energized, sample atoms will rise in the graphite furnace through the source image of the slit and therefore in the path of radiation which is actually detected by the detector.

If the sample material is not deposited centrally in the graphite furnace, but slightly to one side, the possibility exists that when the graphite furnace is heated, the sample atoms will travel vertically upwards and miss the source image of the slit and therefore not fall within the path of radiation which is actually detected by the detector. Thus, those sample atoms will not be detected, thereby resulting in improper or, in fact, no analysis result of the sample material.

The slit in the monochromater which allows the radiation to pass into the monochromater is required in order to block out unwanted wavelengths and also to prevent the detector from detecting extraneous radiation which may completely smother wavelengths which the detector desires to detect. In particular, with a graphite furnace, since the graphite furnace is heated to high temperature and glows white hot, the slit is required to be positioned so that it does not allow imaging of radiation produced from the graphite furnace itself onto the detector, which would otherwise saturate the detector and prevent proper analysis of radiation which passes through the sample and which is produced by the cathode tube. To prevent extraneous radiation from being detected by the detector, the size of the slit is changed depending on the wavelength being detected and also, in some instances, the slit is masked to reduce the length of the slit to ensure that radiation which is produced by the graphite furnace itself is not received by the detector.

Thus, the fact that the masked slit only allows part of the radiation which passes through the sample to enter the monochromater and the orientation of the slit can therefore greatly reduce the sensitivity of the spectrometer.

SUMMARY OF THE INVENTION

The object of the present invention is to provide an atomic absorption spectrometer which overcomes the above problem.

The invention may be said to reside in an atomic absorption spectrometer including:
a monochromater;
an optical path for receiving radiation from a source and for directing the radiation to the monochromater;
a sample station in the optical path;
the monochromater having an entrance slit and a diffraction grating;
a detector for receiving radiation from the monochromater; and
the monochromater being oriented such that the entrance slit is arranged transverse to the vertical so that an image of the slit at the sample station, if radiation passes from the detector along the optical path, is transverse to the vertical so that sample materials produced in a graphite furnace will move upwardly from a lower portion of the graphite furnace and across the transversely arranged image of the slit so that radiation emanating from the source and travelling along the optical path will pass through the sample material and be detected by the detector.

Since the monochromater is oriented such that the entrance slit is arranged transverse to the vertical, sample material which is loaded into the graphite furnace and which merely sits on the lower internal surface of the furnace, will produce sample atoms when the furnace is energized which will pass upwardly, and must cross over the image of the slit and therefore will be located in the path of the radiation which is actually detected by the detector. Thus, the sample material will be detected rather than missing the radiation which is detected by the detector thereby ensuring more complete analysis of sample material and greater sensitivity of the instrument.

Preferably the entrance slit is arranged horizontal or perpendicular to the vertical.

In one embodiment of the invention the optical path includes magnifying means for magnifying the beam of radiation so that the image of the slit at the sample stage has an increased dimension in the direction perpendicular to the horizontal, or in other words, in the vertical direction, thereby increasing the amount of time that sample atoms pass through the radiation which is detected by the detector and further increasing the sensitivity of the spectrometer.

In the preferred embodiment of the instrument the optical path is defined by a plurality of mirrors, some of which are toric mirrors for directing the radiation from the source, to the sample stage and then to the entrance slit of the monochromater.

Preferably the magnifying means is comprised of a first portion of the optical path in which the radiation travels from the sample stage to a beam focusing element, being greater than the length of a second portion of the optical path from the focusing element to the slit.

Preferably the radiation emanating from the source is focused at the sample stage by a primary focusing element.

Preferably the primary focusing element includes at least one toric mirror.

Preferably the beam focusing element comprises a further toric mirror.

Preferably the monochromater also includes a monochromater mirror for reflecting radiation received through the slit to the diffraction grating and for receiving radiation reflected from the diffraction grating, an exit slit in registry with the detector so that the radiation reflected from the monochromater mirror after reflection from the diffraction grating passes through the exit slit to the detector.

The invention may also be said to reside in an atomic absorption spectrometer including:
a monochromater;
an optical path for receiving radiation from a source and for directing the radiation to the monochromater;
a sample station in the optical path;
the monochromater having an entrance aperture and a diffraction grating;
a detector for receiving radiation from the monochromater; and
magnifying means in the optical path for magnifying an image of the aperture at the sample station if radiation passes from the detector along the optical path, to thereby increase the amount of radiation which is focused at the sample stage and which is then passed through the aperture and received by the detector.

According to this aspect of the invention, since the magnifying means effectively magnifies the image of the aperture, more of the radiation which is actually focused at the sample stage is eventually received by the detector to thereby increase sensitivity and reduce the likelihood that some of the sample material produced in a graphite furnace will not travel into the beam of radiation travelling along the optical path from the source. Preferably the magnifying means is comprised of a first portion of the optical path in which the radiation travels from the sample stage to a beam focusing element, being greater than the length of a second portion of the optical path from the focusing element to the slit.

Preferably the radiation emanating from the source is focused at the sample stage by a primary focusing element.

Preferably the primary focusing element includes at least one toric mirror.

Preferably the beam focusing element comprises a further toric mirror.

The invention may also be said to reside in an atomic absorption spectrometer including:
a monochromater;
an optical path for receiving radiation from a source and for directing the radiation to the monochromater;
a sample station in the optical path;
the monochromater having an entrance aperture and a diffraction grating;
a detector for receiving radiation from the monochromater; and
focusing means in the optical path for producing a focal point if radiation passes from the detector along the optical path at a location other than at the sample station and the source so an enlarged out of focus image of the entrance slit is produced at the sample station.

According to this aspect of the invention, since the focusing means focuses the radiation between the sample station and the source, an enlarged out of focus image of the entrance slit will occur at the sample stage, thereby increasing the amount of radiation which is actually detected by the detector. Although the image of the entrance slit would be out of focus at the sample station, this has no bearing on the atomic absorption characteristics of the radiation and sample and therefore, no bearing on the detection of the radiation by the detector and the analysis by the atomic absorption spectrometer. However, since the entrance slit is effectively magnified at the sample station, again the invention reduces the likelihood that the sample material produced in a graphite furnace at the sample station will not travel into the beam of radiation detected by the detector.

The location of the focus can be between the sample station and the source or between the sample station and the monochromater. In the preferred embodiment of the invention, the focal point is at a location between the sample station and the source.

Preferably the optical path includes at least one toric mirror and the toric mirror has a curvature such as to create a focus for radiation passing back from the detector to the source along the optical path, at the location between the sample station and the source.

This aspect of the invention may be used instead of or in combination with the previously described aspects of the invention.

BRIEF DESCRIPTION OF THE DRAWINGS

A preferred embodiment of the invention will be described, by way of example, with reference to the accompanying drawings in which:

With reference to FIG. 1, the relevant components of the atomic absorption spectrometers of the present invention are shown in their preferred form. The spectrometer includes a hollow cathode lamp 10 for producing electromagnetic radiation 12 at a predetermined wavelength. In general, a plurality of lamps 10 will be arranged in a carousel (not shown) and sequentially moved into the position shown in FIG. 1 so that each can be energized to produce a beam of light 12 of a particular wavelength which will pass through a sample material and then be detected to enable the sample material to be analysed.

Figure 1:
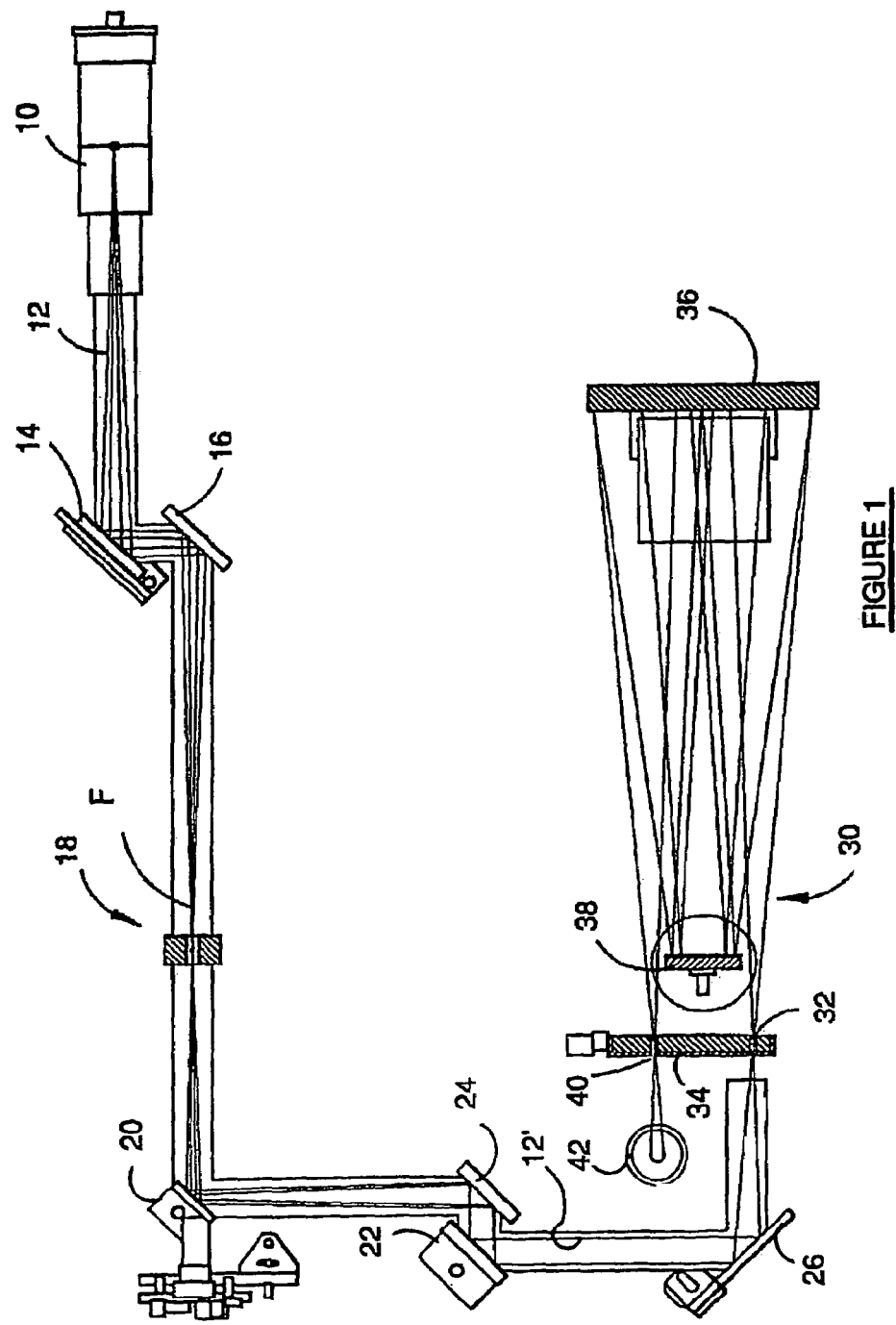
FIG. 1 is a schematic view of an atomic absorption spectrometer embodying the invention.

A toric mirror 14 receives the radiation 12 from the lamp 10 and reflects the radiation to a flat mirror 16. The flat mirror 16 reflects the radiation to a sample stage 18 and focuses the radiation 12 at the sample stage 18 so the radiation will pass through sample atoms produced at the sample stage 18.

The cathode tubes 10 generally include a 3 mm diameter source and therefore the radiation focused at the sample stage 18 is generally a 3 mm diameter spot at the sample stage 18.

Radiation which passes through the sample stage 18 is reflected by a flat mirror 20 to a flat mirror 24 which then reflects the radiation to a toric mirror 22. The toric mirror 22 reflects the radiation to a further toric mirror 26 which reflects the radiation to a monochromater 30. The monochromater 30 includes an entrance aperture in the form of a slit 32 (best shown in FIG. 1A) which is provided in an end plate 34 of the monochromater 30. The monochromater has a monochromater mirror 36 which reflects the radiation to a diffraction grating 38 which in turn reflects the radiation back to the monochromater mirror 36 for reflection through an exit slit 40 to detector 42.

The toric mirror 14 focuses the beam of radiation 12 at the sample stage 18 and the beam of radiation which passes from the sample stage 18 and received by the toric mirror 22 leaves the toric mirror 22 as a parallel beam of radiation 12'. The beam 12' is reflected by the toric mirror 26 and focused at the entrance slit 32. The beam path from the sample stage 18 to the toric mirror 22 is greater than the beam path from the toric mirror 26 to the slit 32, thereby amplifying or magnifying the radiation. Thus, the different length of the beam paths between the focus at the sample stage 18 and the toric mirror 22 and from the toric mirror 26 to the focus at the slit 32 acts as an amplifier or magnifier when viewed back from the detector 42, the purpose of which will be described in more detail hereinafter.

The sample stage 18 may include an apparatus for producing sample atoms of any particular type. However, the present invention has particular application to spectrometers which include a graphite furnace 37 for the production of sample atoms. The graphite furnace is shown in FIG. 4 in side view and end views of the furnace are shown in FIGS. 2 and 3.

Figure 2:
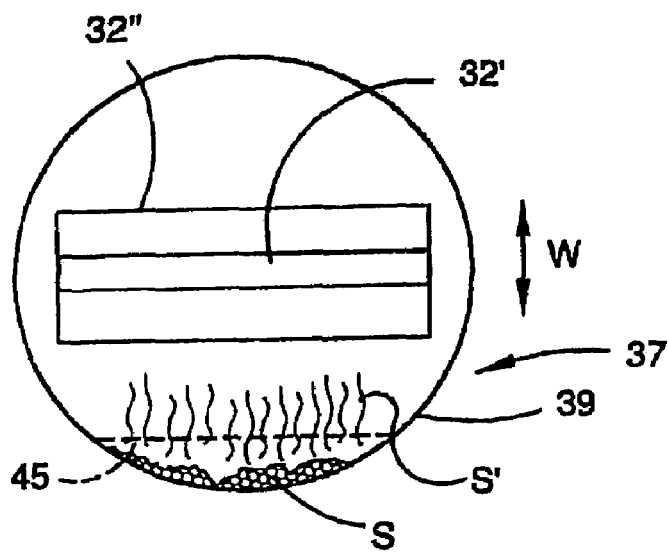
FIG. 2 is a schematic view of an end view of a graphite furnace showing the image of an entrance slit of a monochromater illustrating the preferred embodiment of the invention.
Figure 4:
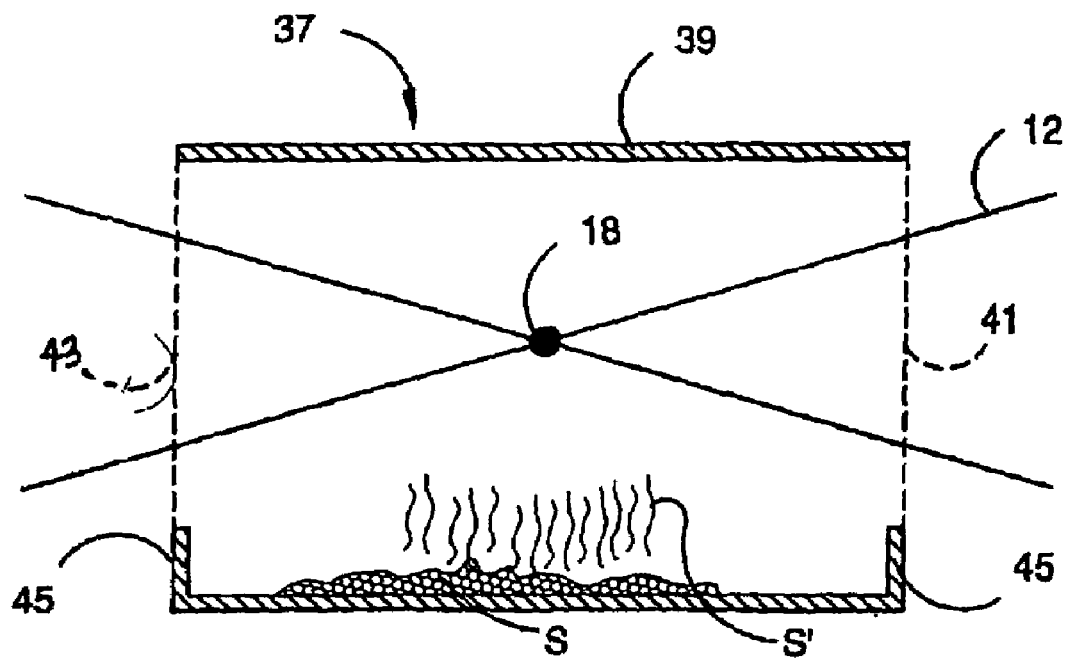
FIG. 4 is a side view of a graphite furnace which can be used in the preferred embodiment of the invention.

With reference to FIGS. 2 and 4, the furnace generally comprises a tube 39 of graphite which has a circular cross section as shown in FIG. 2. The ends 41 and 43 of the tube 39 are open and the radiation 12 can pass through the tube 39 and be focused at point 18 shown in FIG. 4 which defines the sample stage referred to in FIG. 1 and then travels to the mirror 20.

The graphite furnace 37 can include dam walls 45 at each end which act to retain sample material deposited in the furnace from flowing out the open ends 41 and 43.

Figure 3:
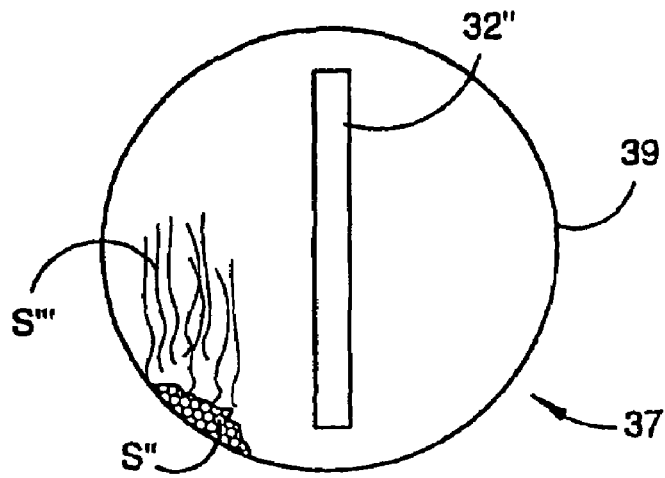
FIG. 3 is a view similar to FIG. 2 but of a conventional arrangement.

When the graphite furnace is heated, sample atoms are generated which pass vertically upward from the sample deposited in the furnace as represented by reference S' in FIGS. 2 and 3 towards the upper portion of the furnace.

Figure 1A:
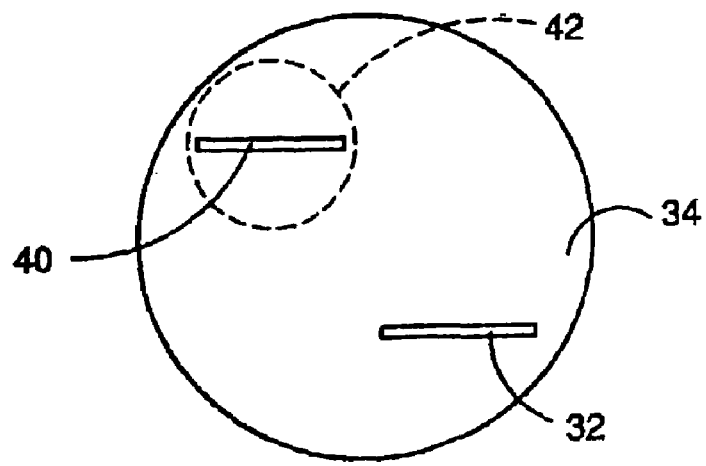
FIG. 1A is a cross-sectional view along the line 1A-1A of FIG. 1.

As shown with reference to FIG. 1A, the entrance slit 32 is oriented so that it is substantially horizontal as best shown in FIG. 1A. Thus, the image of the slit 32 at the sample stage 18 is a horizontal slit 32' as shown in FIG. 2. Thus, when the sample material S' passes upwardly in the furnace 37, the sample material will cross over the slit 32' thereby ensuring that radiation which passes through the sample stage 18 and is eventually received by the detector 42 will in fact pass through the sample material S' generated by the furnace 37.

When considering an image of the slit 32 at the sample stage 18, it is conventional to think of the image in terms of directing radiation from the detector 42 back through the monochromater 30 and along the optical path of the beam 12 to the sample stage 18. If radiation or light is shone in that direction from the detector 42, then an image of the slit 32 will appear at the sample stage 18 and will effectively define the area of the sample stage 18 through which radiation actually passes from the tube 10 and which is actually detected by the detector 42.

FIG. 3 shows the orientation of the slit 32 of a conventional atomic absorption spectrometer as imaged at the sample stage 18. It can be seen that the slit 32' in FIG. 3 is vertically oriented and therefore sample material S", incorrectly deposited in the furnace 37, will generally move vertically upward as shown by lines S''' and can well miss the radiation 12 passing through the furnace 37 and which will actually be detected by the detector 42. However, as illustrated with reference to FIG. 2, the fact that the slit 32 in the preferred embodiment is oriented such that the image is horizontal rather than vertical means that sample material, regardless of where it is deposited in the furnace 37 will rise upwardly and cross over the slit 32 thereby ensuring that radiation which passes through the sample stage 18 and which is actually detected by detector 42, will pass through the sample material S' generated by the furnace 37.

In order to orient the slit 32 in the horizontal orientation rather than the vertical orientation, the entire monochromater 30 of a conventional atomic or absorption spectrometer can be thought of as being rotated 90° from its normal position. Thus, not only is the slit 32 arranged horizontally, the diffraction grating 32 is also rotated so as to be in alignment with the radiation passing through the slit 32 so that the diffraction grating can separate the wavelength passing through the slit 32 and then direct those wavelengths to the mirror 36 for reflection through the horizontal exit slit 40 to the detector 42.

The amplification of the beam 12 produced by the difference in path length from the sample stage 18 to the mirror 22, compared to the length of the path length from the mirror 26 to the path 32, produces a widening of the image of the slit 32 at the sample stage 18 as shown by double-headed arrow W in FIG. 2 so as to produce a much wider image of the slit as shown by reference 32" in FIG. 2. The result of this is that sample material passing upwardly in the furnace 37 will remain longer in the image of the slit 32 at the sample stage thereby increasing the likelihood of impingement with radiation from the tube 10 and therefore increase of the sensitivity of the spectrometer.

The increase in width W of the image of the slit 32 means that the actual area through which radiation passes is much closer to the actual 3 mm diameter spot of radiation which is focused at the sample stage 18 and therefore considerably less radiation is lost than is the case when compared to conventional arrangements.

Because of the magnification of the image of the slit produced by the difference in path lengths from the sample stage 18 to the mirror 22, compared to the length of the path from the mirror 26 to the slit 32, the mirror 36 is slightly larger than a conventional monochromater mirror to ensure that it does receive all the radiation passing through the slit 32 and therefore reflects all the radiation to the diffraction grating 38 and then reflects all the radiation from the diffraction grating 38 to the exit slit 40 for detection by the detector 42.

The preferred embodiment of the invention therefore provides an atomic absorption spectrometer which is particular useful with a graphite furnace and which can not only increase sensitivity of the instrument but also ensure that radiation which is received by the detector 42 will actually pass through the sample material generated by the furnace when the furnace is heated. Thus, more reliable analysis results can be obtained with greater sensitivity of the instrument.

Figure 5:
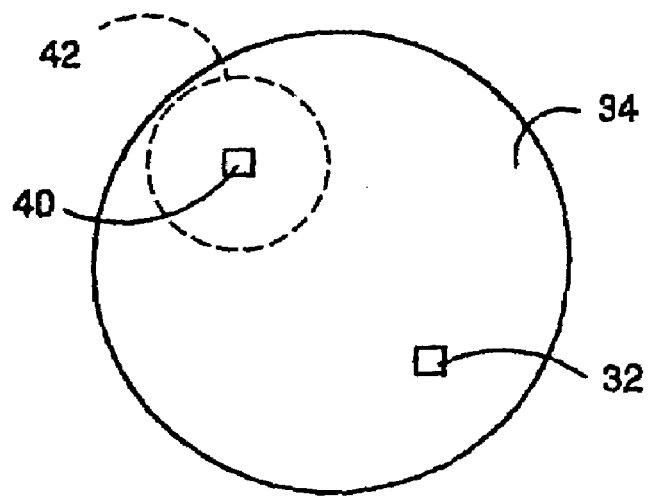
FIG. 5 and FIG. 6 are views similar to FIGS. 1A and 2 showing a further embodiment.
Figure 6:
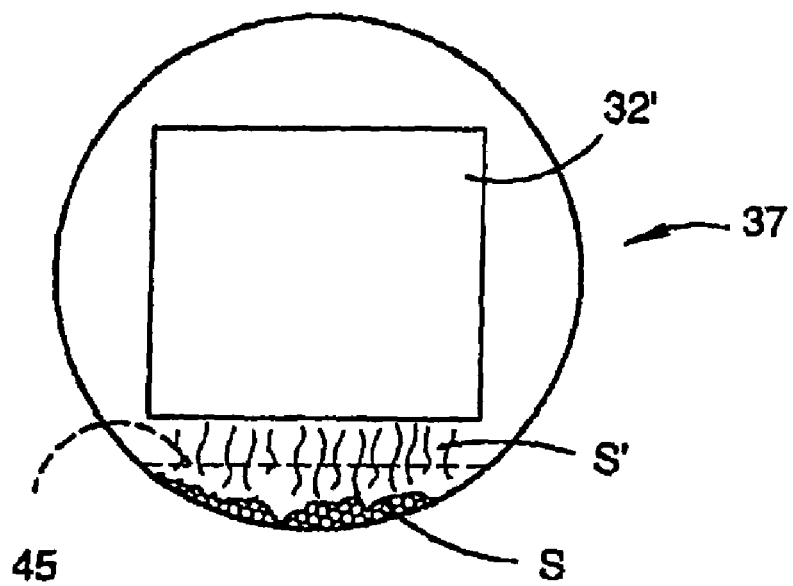

FIGS. 5 and 6 show a second embodiment in which the entrance aperture and exit aperture are in the form of a square 32. The aperture 32 results in a magnified image of the square aperture at the sample stage, as is shown in FIG. 6. The configuration of the aperture could be other shapes and the fact that the image of the aperture will be magnified at the sample stage 18 means more radiation will be received by the detector 42. The configuration of the aperture 32 will change (as will the configuration of the slit aperture in FIGS. 1 to 4) under control of the spectrometer to filter out unwanted wavelengths from entering the monochromater 30. However, regardless of the shape or size of the aperture, the image of the aperture at the sample stage will be enlarged so more radiation passing through the sample is collected by the detector 42. The maximum size of the aperture image is preferably within the confines of the furnace 37, as shown in FIGS. 2 to 5, so radiation produced by the heated furnace 37 is not received by the detector 42.

In the embodiment shown with reference to the drawings the mirrors 14 and 16 and the mirrors 22 and 24 are arranged such that the reflection of the beam 12 is generally at right angles. However, in other embodiments, the mirrors could be arranged such that the reflection is not at right angles and the radiation is reflected from the mirrors 14 and 24 at an obtuse angle with respect to the incoming beam 12 to the mirrors 16 and 24. Thus, rather than the beam 12 having a right angled configuration at the mirrors 14, 16 and 22, 24, the beam has a zigzagged shape.

Furthermore, in other embodiments, rather than the toric mirror 14 being provided before the flat mirror 16, the order of these mirrors may be reversed as may the order of the mirrors 22 and 24.

Figure 7:
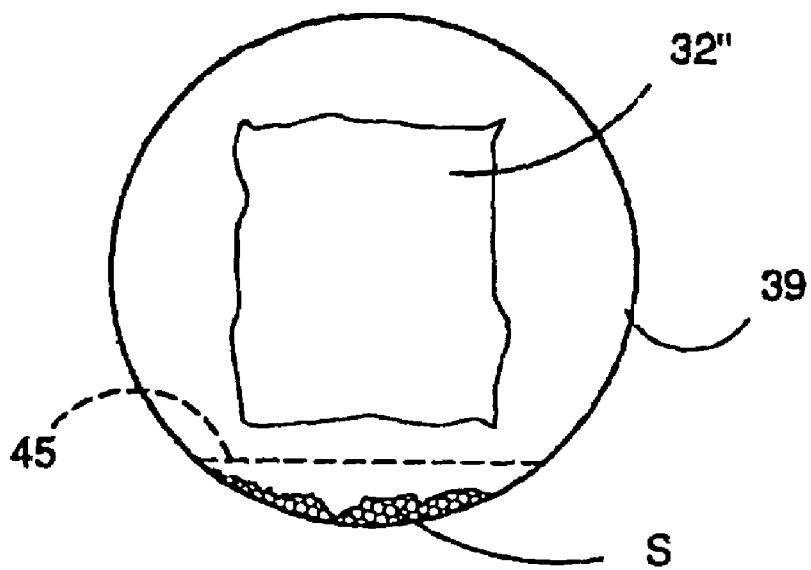
FIG. 7 is a view of a further embodiment of the invention.

FIG. 7 shows a further embodiment of the invention in which like reference numerals indicate like parts to those previously described.

In the embodiment of FIG. 7, the toric mirror 22 is changed so that if light was to emanate back from the detector 42 along the optical path, the light would be focused at point F, which is not at the sample station 18, as in the embodiment of FIG. 1 but, rather, at a position between the sample station 18 and the light source 10. Most preferably, the distance between the focal point F and the station 18 would be in the order of 15 to 25 mm. The focusing of the light at the point F results in an enlarged image of the slit 32 at the sample station 8 albeit an out of focus image of the slit. However, because the image of the slit is enlarged at the station 18, the detector will detect more radiation passing through the graphite furnace at the station 18 as shown by the image 32" in FIG. 7. The fact that the image of the slit 32 is out of focus at the sample station 18 has no bearing, on the atomic absorption characteristics of the radiation or on the analysis performed by the detected radiation. However, as is apparent from a consideration of FIG. 7, the image of the slit 32 is much larger at the sample station S than the conventional technique, thereby ensuring that a larger region of radiation is available in which sample material can move and intercept the light beam from the source 10 travelling to the detector 42. Thus, the characteristics of the spectrometer are improved in the same manner as described with reference to FIGS. 1 to 6.

The embodiment of FIG. 7 can be used instead of or in combination with the arrangements described with reference to FIGS. 1 to 6.

Since modifications within the spirit and scope of the invention may readily be effected by persons skilled within the art, it is to be understood that this invention is not limited to the particular embodiment described by way of example hereinabove.

The invention claimed is:

1. An atomic absorption spectrometer including:
a monochromater;
an optical path for receiving radiation from a source and for directing the radiation to the monochromater;
a sample station in the optical path;
the monochromater having an entrance aperture and a diffraction grating;
a detector for receiving radiation from the monochromater; and
magnifying means in the optical path for magnifying an image of the aperture at the sample station if radiation passes from the detector along the optical path, to thereby increase the amount of radiation which is focused a the sample stage and which is then passed through the aperture and received by the detector.

2. The spectrometer of claim 1 wherein the magnifying means is comprised of a first portion of the optical path in which the radiation travels from the sample stage to a beam focusing element, being greater than the length of a second portion of the optical path from the focusing element to the slit.

3. The spectrometer of claim 2 wherein the radiation emanating from the source is focused at the sample stage by a primary focusing element.

4. The spectrometer of claim 3 wherein the primary focusing element includes at least one toric mirror.

5. The spectrometer of claim 4 wherein the beam focusing element comprises a further toric mirror.

6. An atomic absorption spectrometer including:
a monochromater;
an optical path for receiving radiation from a source and for directing the radiation to the monochromater;
a sample station in the optical path;
the monochromater having an entrance aperture and a diffraction grating;
a detector for receiving radiation from the monochromater; and
focusing means in the optical path for producing a focal point if radiation passes from the detector along the optical path at a location other than at the sample station and the source so an enlarged out of focus image of the entrance slit is produced at the sample station.

7. The spectrometer of claim 6 wherein the location of the focus is between the sample station and the source.

8. The spectrometer of claim 6 wherein the optical path includes at least one toric mirror and the toric mirror has a curvature such as to create a focus for radiation passing back from the detector to the source along the optical path, at the location between the sample station and the source.

9. The spectrometer of claim 6 wherein the location of the focus is between the sample station and the monochromater.

* * * * *